(12) United States Patent
Li et al.

(10) Patent No.: US 10,533,148 B2
(45) Date of Patent: Jan. 14, 2020

(54) MEMBRANE PHOTOBIOREACTOR FOR TREATING NITROGEN AND PHOSPHORUS THAT ARE OUT OF LIMITS IN BIOGAS SLURRY AND TREATING METHOD THEREOF

(71) Applicant: XIAMEN UNIVERSITY, Xiamen (CN)

(72) Inventors: Qingbiao Li, Xiamen (CN); Xi Chen, Xiamen (CN); Ning He, Xiamen (CN); Yuanpeng Wang, Xiamen (CN); Liang Shen, Xiamen (CN); Haitao Wang, Xiamen (CN)

(73) Assignee: XIAMEN UNIVERSITY, Xiamen (CN)

( * ) Notice: Subject to any disclaimer, the term of this patent is extended or adjusted under 35 U.S.C. 154(b) by 133 days.

(21) Appl. No.: 15/306,398

(22) PCT Filed: Jul. 30, 2014

(86) PCT No.: PCT/CN2014/083294
§ 371 (c)(1),
(2) Date: Oct. 24, 2016

(87) PCT Pub. No.: WO2015/161577
PCT Pub. Date: Oct. 29, 2015

(65) Prior Publication Data
US 2017/0044474 A1 Feb. 16, 2017

(30) Foreign Application Priority Data

Apr. 25, 2014 (CN) .......................... 2014 1 0169909

(51) Int. Cl.
*C12M 1/00* (2006.01)
*B01D 69/08* (2006.01)
(Continued)

(52) U.S. Cl.
CPC ............. *C12M 21/02* (2013.01); *B01D 69/08* (2013.01); *C02F 1/44* (2013.01); *C02F 3/102* (2013.01);
(Continued)

(58) Field of Classification Search
CPC .................... B01D 69/08; B01D 63/02; B01D 2311/2688; C02F 1/44; C02F 2103/22;
(Continued)

(56) References Cited

U.S. PATENT DOCUMENTS 5,286,646 A * 2/1994 Kearns ................... C12M 29/16
435/400
5,605,835 A * 2/1997 Hu .......................... A61F 2/022
435/297.2

(Continued)

FOREIGN PATENT DOCUMENTS

CN     101892268 A    11/2010
CN     101921811 A    12/2010
(Continued)

OTHER PUBLICATIONS

AISIMO, What is a KD (kiloDalton), Oct. 23, 2013.*
(Continued)

*Primary Examiner* — Nam X Nguyen
*Assistant Examiner* — Julia L. Wun
(74) *Attorney, Agent, or Firm* — Seed Intellectual Property Law Group LLP

(57) ABSTRACT

A membrane photobioreactor for treating nitrogen and phosphorus that are out of limits in a biogas slurry and treating method thereof, relating to biogas slurry treatment. The membrane photobioreactor for treating nitrogen and phosphorus that are out of limits in a biogas slurry is provided with a biogas slurry storage tank, peristaltic pumps, a microalgae cultivating tank, an air pump, a membrane (Continued)

photobioreactor and a hollow fiber membrane. The biogas slurry containing nitrogen and phosphorus that are out of limits is stored in the biogas slurry storage tank, and is driven by a first peristaltic pump to circularly flow in a silicone pipe; a microalgae solution is cultivated under illumination in the microalgae cultivating tank, and is driven by a second peristaltic pump to circularly flow in a silicone pipe, air is fed into the microalgae cultivating tank through the air pump, the biogas slurry and the microalgae solution are converged in the membrane photobioreactor, and the biogas slurry circularly flows inside the hollow fiber membrane pipe and the microalgae solution circularly flows outside the hollow fiber membrane pipe, the two being in a cross flow; and the nitrogen and phosphorus that are out of limits in the biogas slurry penetrate from the inside of the hollow fiber membrane and are absorbed by the microalgae solution outside the membrane, and after cyclical cultivation, nitrogen and phosphorus that are out of limits in the biogas slurry are absorbed, and the discharge standards are achieved.

3 Claims, 3 Drawing Sheets

(51) Int. Cl.
C02F 3/12 (2006.01)
C02F 3/32 (2006.01)
C12M 1/12 (2006.01)
C02F 101/10 (2006.01)
C02F 101/16 (2006.01)
C02F 1/44 (2006.01)
C02F 3/10 (2006.01)
C02F 103/22 (2006.01)

(52) U.S. Cl.
CPC ............ *C02F 3/1273* (2013.01); *C02F 3/322* (2013.01); *C12M 25/10* (2013.01); *C12M 29/00* (2013.01); *B01D 2311/2688* (2013.01); *C02F 2101/105* (2013.01); *C02F 2101/16* (2013.01); *C02F 2103/22* (2013.01); *C02F 2203/006* (2013.01)

(58) Field of Classification Search
CPC .............. C02F 2203/006; C02F 3/1268; C02F 3/1273; C02F 3/102; C02F 3/322; C02F 2101/105; C02F 2101/16; C12M 21/02; C12M 21/04; C12M 23/58; C12M 25/10; C12M 29/16; C12M 29/00; Y02W 10/15; Y02W 10/37; Y02E 50/343
USPC .. 210/602, 195.1, 321.87, 500.23, 906, 903, 210/172.1, 172.2
See application file for complete search history.

(56) References Cited

U.S. PATENT DOCUMENTS

| | | | |
|---|---|---|---|
| 7,186,339 B1* | 3/2007 | Roos | A01C 3/023 210/603 |
| 7,641,796 B2* | 1/2010 | Stroot | C02F 11/04 210/603 |
| 2011/0247977 A1 | 10/2011 | Song et al. | |

FOREIGN PATENT DOCUMENTS

| | | | | |
|---|---|---|---|---|
| CN | 103007741 A | 4/2013 | | |
| CN | 103789195 A | 5/2014 | | |
| CN | 103910434 A | 7/2014 | | |
| WO | WO-2008010737 A1 * | 1/2008 | ............ | C12M 21/02 |
| WO | 2010/020989 A1 | 2/2010 | | |
| WO | WO-2012019338 A1 * | 2/2012 | ................ | C02F 3/28 |

OTHER PUBLICATIONS

Cole-Parmer, Masterflex tubing options, 2017.*
Chen et al., "Developments in the Ecological Treatment of Biogas Slurry," China Academic Journal Electronic Publishing House, Article ID:0528-9017, 2010, 4 pages (with English Abstract).
Cho et al., "Reuse of effluent water from a municipal wastewater plant in microalgae cultivation for biofuel production," *Bioresource Technology* 102:8639-8646, 2011.
Honda et al., "Carbon dioxide capture and nutrients removal utilizing treated sewage by concentrated microalgae cultivation in a membrane photobioreactor," *Bioresource Technology* 125:59-64, 2012.
Singh et al., "Nutrient removal from membrane bioreactor permeate using microalgae and in a microalgae membrane photoreactor," *Bioresource Technology* 117:80-85, 2012.

* cited by examiner

MEMBRANE PHOTOBIOREACTOR FOR TREATING NITROGEN AND PHOSPHORUS THAT ARE OUT OF LIMITS IN BIOGAS SLURRY AND TREATING METHOD THEREOF

CROSS-REFERENCE TO RELATED APPLICATION

This application is a U.S. national phase application of International Application No. PCT/CN2014/083294 filed on Jul. 30, 2014, which claims priority benefit of Chinese Patent Application No. 201410169909.X filed on Apr. 25, 2014. The contents of all of these specifications are incorporated by reference herein in their entirety.

FIELD OF THE INVENTION

The present invention relates to biogas slurry treatment, and specifically relates to a membrane photobioreactor for treating nitrogen and phosphorus that are out of limits in biogas slurry and treating method thereof.

DESCRIPTION OF THE PRIOR ART

The biogas slurry generated subsequent to anaerobic fermentation with various organic wastes has large amount of inorganic salt components such as ammonia nitrogen, phosphates, and the like. If directly discharged into rivers, they can not only cause water eutrophication, but also cause the loss of large amount of beneficial nutrients. At present, biogas slurry treatment technologies can be divided into 2 main classes: the first one is aerobic microorganism treating method, the second one is natural biological treating method. Aerobic treating methods comprise activated sludge method, biofilter, bio disc contact oxidation method and batch type activated sludge method and the like. Their process structures are complicated, the quantity of mechanical equipments is large, maintenance workload is large, investment is large, energy consumption is high, operating and maintenance fees are high, small-scale farms are difficult to bear them, which does not adapt to the economic development level of our country. Natural biological treating methods mainly comprise: biological pond method and constructed wetlands treating method. Biological pond technology fits the situation of our country, but there are also many problems, including unreasonable structure of biological pond, low purification load, the universal siltation problem and the like. Wetlands treating method occupies large area, which is hard to be actually applied in the regions lack of lands (Journal of Zhejiang Agricultural Sciences, 2010, 4, 872-874).

Algae have unique metabolic ways, and can use solar energy and inorganics to synthesize their own protoplasm by photosynthesis, overcoming the drawbacks that the traditional sewage treating methods not only prone to cause secondary pollution, but also cause the loss of valuable potential nutrients and can cause incomplete use of sources. Algae can remove nutrients of nitrogen and phosphorus etc causing water eutrophication effectively and cheaply. As a substituting or remedying method of secondary treating or deep treating sewage, the use of algae for denitrification and dephosphorization has attracted broad attention. Whereas, biogas slurry generally comprises large amount of microorganisms and suspended matters, only a few algae species can grow therein normally. If the majority of commercial algae species are directly put into the biogas slurry to perform the absorption of nutrients of nitrogen and phosphorus etc, their growth will be subjected to inhibition to different degrees (Bioresour. Technol, 2011, 102, 8639-8645). A recent study combines the photobioreactor for culturing microalgae and hollow fiber membrane, but it merely plays a role of enrichment and increasement of algae concentration. To achieve the aim of increasing the absorption rate of nitrogen and phosphorus, only pure culture solution can be used as the culture medium (Bioresour. Technol 2012, 117, 80-85; Bioresour. Technol, 2012, 125, 59-64).

In order to enhance the absorption rate of microalgae to the nutrients of nitrogen and phosphorus etc, and to enhance the yield of commercial algae species, it requires pretreating the biogas slurry in advance to remove the microorganisms and suspended matters therein. At present the common pretreating methods are centrifugation of biogas slurry, membrane filtration or ultraviolet irradiation sterilization (Bioresour. Technol, 2011, 102, 8639-8645), but they can only treat a small amount of biogas slurry, and the energy consumption is comparatively large, it can merely be applied in laboratories, and cannot be used on a large scale, which becomes the main barrier restricting the promotion and application of the technique that microalgae make use of biogas slurry.

In addition, in traditional methods, whenever the treatment of a batch of biogas slurry completes, it requires replacing with new biogas slurry and reloading algae seeds for enlarged culture, which makes the microalgae cannot be maintained at a high concentration, thereby decreases the amount of nitrogen and phosphorus absorbed by the microalgae in biogas slurry, and extents the time of treating biogas slurry.

SUMMARY OF THE INVENTION

The purpose of the present invention is to provide a membrane photobioreactor for treating nitrogen and phosphorus that are out of limits in biogas slurry that can achieve the purpose of reducing the inhibition of harmful substance to microalgae enhancing the absorption of microalgae to the nutrients of nitrogen and phosphorus and the like.

Another purpose of the present invention is to provide a method for treating nitrogen and phosphorus that are out of limits in biogas slurry.

The membrane photobioreactor for treating nitrogen and phosphorus that are out of limits in biogas slurry is provided with a biogas slurry storage tank, a first peristaltic pump, a microalgae cultivating tank, a second peristaltic pump, an air pump, a membrane photobioreactor and a hollow fiber membrane; an air outlet of the air pump is connected to the microalgae cultivating tank, the hollow fiber membrane is embedded in the membrane photobioreactor, an outlet of the microalgae cultivating tank is connected to an inlet and an outlet at side ends of the membrane photobioreactor, an inlet of the second peristaltic pump is connected to the outlet of the membrane photobioreactor, an outlet of the second peristaltic pump is connected to the microalgae cultivating tank, microalgae flows circularly between the microalgae cultivating tank and the membrane photobioreactor driven by the second peristaltic pump, and microalgae is on the outer side of the hollow fiber membrane in the membrane photobioreactor; the slurry storage tank is connected to an inlet and an outlet at upper and lower ends of the membrane photobioreactor, biogas slurry flows circularly between the biogas slurry storage tank and the membrane photobioreactor driven by the first peristaltic pump, and biogas slurry is on the inner side of the hollow fiber membrane in the membrane photobioreactor.

The biogas slurry storage tank is connected to the inlet and the outlet at upper and lower ends of the membrane photobioreactor via silicone tubes with diameter of 6 mm.

The microalgae cultivating tank is connected to the inlet and the outlet at side ends of the membrane photobioreactor via silicone tubes with diameter of 6 mm.

Air is compressed and fed into the microalgae cultivating tank by the air pump via silicone tubes with diameter of 6 mm.

The membrane photobioreactor is a cylindrical photobioreactor, and the height-to-diameter ratio thereof can be 6~7.

The hollow fiber membrane can adopt 0.1 μm hollow fiber membrane.

A method for treating nitrogen and phosphorus that are out of limits in biogas slurry, using the membrane photobioreactor for treating nitrogen and phosphorus that are out of limits in biogas slurry, the method is as follows:

The biogas slurry containing nitrogen and phosphorus that are out of limits is stored in the biogas slurry storage tank, and flows circularly inside the silicone tubes driven by the first peristaltic pump; microalgae solution is cultured under illumination in the microalgae cultivating tank, and flows circularly inside the silicone tubes driven by the second peristaltic pump, air is fed into the microalgae cultivating tank through the air pump, biogas slurry and microalgae solution are converged in the membrane photobioreactor, biogas slurry flows circularly inside the tube of the hollow fiber membrane, microalgae solution flows circularly outside the tube of the hollow fiber membrane, the two being in a cross flow; the nitrogen and phosphorus that are out of limits in biogas slurry penetrate through the hollow fiber membrane and absorbed by microalgae solution outside the membrane, the nitrogen and phosphorus that are out of limits in biogas slurry are absorbed via cyclical cultivation to achieve the discharge standards, at completion of the absorption of the nitrogen and phosphorus in biogas slurry in the storage tank, it only requires replacing with new biogas slurry in the biogas slurry storage tank without replacing microalgae in the microalgae cultivating tank.

The biogas slurry can be the waste liquid generated after the anaerobic fermentation of straw and pig manure producing biogas, the waste liquid generally contains up to 1000 mg/L of ammonia nitrogen and 5 g/L of solid suspended matters.

The circulation flow velocity of the biogas slurry flowing circularly inside the silicone tubes driven by the first peristaltic pump can be 40~60 mL/min;

The circulation flow velocity of the microalgae solution flowing circularly inside the silicone tubes driven by the second peristaltic pump can be 120~160 mL/min.

The amount of the fed air can be 1 L/L·min.

The present invention solves the problem that harmful substances like microorganisms and suspended matters etc in biogas slurry inhibit the growth of microalgae, and meanwhile maintains high concentration of microalgae to expedite biogas slurry processing rate. The present invention achieves the purpose of reducing the inhibition of harmful substances to microalgae, and enhancing the absorption of microalgae to the nutrients of nitrogen and phosphorus and the like by means of embedding 0.1 μm hollow fiber membrane into general column type photobioreactor, biogas slurry flows circularly inside the membrane by peristaltic pump, microalgae solution flows circularly outside the membrane by peristaltic pump, the harmful substances of microorganisms and suspended matters larger than the membrane pore size are intercepted, while the nutrients of nitrogen and phosphorus etc are diffused from the biogas slurry to the microalgae through the membrane to be absorbed.

The present invention has the following prominent advantages:

1. Using the characteristics that hollow fiber membrane can intercept substances larger than its pore size, the present invention intercepts harmful substances like microorganisms and suspended matters larger than the pore size, while nutrients of nitrogen and phosphorus etc can penetrate the membrane, achieving the purpose of reducing the inhibition to microalgae and facilitating their growth.
2. It can enable microalgae maintained at comparatively high concentration, enhance the absorption rate of microalgae to nitrogen and phosphorus in biogas slurry, and shorten the time of microalgae for treating biogas slurry.
3. After being treated by microalgae for 18 days, biogas slurry can reach the first grade of the national the discharge standards that contains ammonia nitrogen below 10 mg/L, and phosphates below 0.5 mg/L.

DESCRIPTION OF THE DRAWINGS

In FIG. 1, symbol A is air, B is biogas slurry.

In FIG. 2, symbol ■ is PBR, ● is MPBR.

In FIG. 3, symbol ■ is PBR, ● is MPBR.

DETAILED DESCRIPTION OF THE PREFERRED EMBODIMENTS

The detailed explanation below merely illustrates the general principle of the present invention, but is not restrictive, which can be reasonably adjusted and revised in the process of actual application according to specific conditions of the properties of different algae species, and the discharge standards of different biogas slurry and the like.

Figure 1:
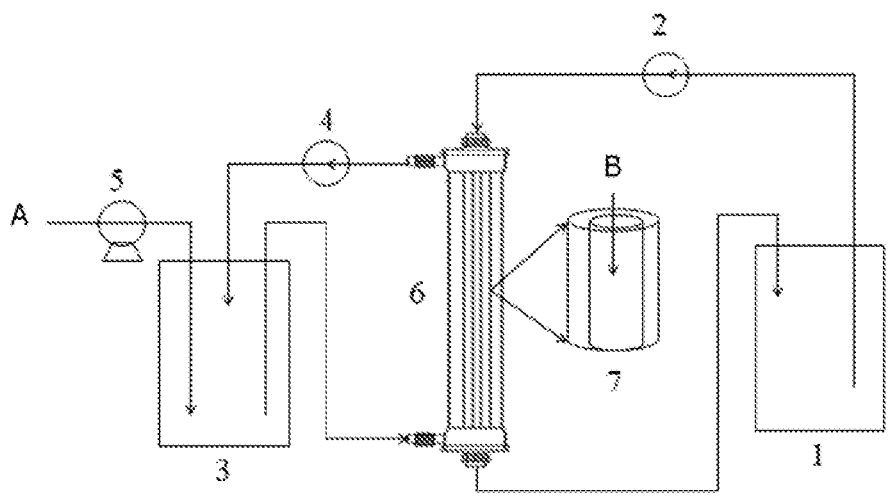
FIG. 1 is the schematic diagram of the structural components of the Example of the membrane photobioreactor for treating nitrogen and phosphorus that are out of limits in biogas slurry of the present invention.

See FIG. 1, the Example of the membrane photobioreactor for treating nitrogen and phosphorus that are out of limits in biogas slurry is provided with a biogas slurry storage tank 1, a first peristaltic pump 2, a microalgae cultivating tank 3, a second peristaltic pump 4, an air pump 5, a membrane photobioreactor 6 and a hollow fiber membrane 7.

The air outlet of air pump 5 is connected to microalgae cultivating tank 3, hollow fiber membrane 7 is embedded in membrane photobioreactor 6, the outlet of microalgae cultivating tank 3 is connected to the inlet at a side end of membrane photobioreactor 6, the inlet of the second peristaltic pump 4 is connected to the outlet of membrane photobioreactor 6, the outlet of the second peristaltic pump 4 is connected to microalgae cultivating tank 3, microalgae flows circularly between microalgae cultivating tank 3 and membrane photobioreactor 6 driven by the second peristaltic pump 4, and microalgae is on the outer side of hollow fiber membrane 7 in membrane photobioreactor 6; slurry storage tank 1 is connected to the inlet and the outlet at upper and lower ends of membrane photobioreactor 6, biogas slurry flows circularly between biogas slurry storage tank 1 and membrane photobioreactor 6 driven by the first peristaltic pump 2, and biogas slurry is on the inner side of hollow fiber membrane 7 in membrane photobioreactor 6. In FIG. 1, symbol A is air, B is biogas slurry.

Biogas slurry storage tank 1 is connected to the inlet and the outlet at upper and lower ends of membrane photobioreactor 6 via silicone tubes with diameter of 6 mm.

Microalgae cultivating tank 3 is connected to the inlet and the outlet at side ends of membrane photobioreactor 6 via silicone tubes with diameter of 6 mm.

Air is compressed and fed into microalgae cultivating tank 3 by air pump 5 via silicone tubes with diameter of 6 mm.

Membrane photobioreactor 6 is a cylindrical photobioreactor, and the height-to-diameter ratio thereof can be 6~7.

Hollow fiber membrane 7 adopts 0.1 μm hollow fiber membrane.

The method of using membrane photobioreactor for treating nitrogen and phosphorus that are out of limits in biogas slurry is as follows:

The biogas slurry containing nitrogen and phosphorus that are out of limits is stored in biogas slurry storage tank 1, and flows circularly inside silicone tubes driven by the first peristaltic pump 2, and the flow rate is 40~60 mL/min; microalgae solution is cultured under illumination in microalgae cultivating tank 3, and flows circularly inside silicone tubes driven by the second peristaltic pump 4, and the flow rate is 120~160 mL/min, 1 L/L·min of air is fed into microalgae cultivating tank 3 through air pump 5, biogas slurry and microalgae solution are converged in membrane photobioreactor 6, biogas slurry flows circularly inside the tube of hollow fiber membrane 7, microalgae solution flows circularly outside the tube of hollow fiber membrane 7, the two being in a cross flow; the nitrogen and phosphorus that are out of limits in biogas slurry penetrate through hollow fiber membrane 7 and absorbed by microalgae solution outside the membrane, the nitrogen and phosphorus that are out of limits in biogas slurry are absorbed via cyclical cultivation to achieve the discharge standards, at completion of the absorption of the nitrogen and phosphorus in biogas slurry in storage tank 1, it only requires replacing with new biogas slurry in biogas slurry storage tank 1 without replacing microalgae in microalgae cultivating tank 3.

Specific examples are provided below.

EXAMPLE 1

In a membrane photobioreactor (membrane biophotoreactor, MPBR) for treating nitrogen and phosphorus that are out of limits in biogas slurry, primarily, the concentration of biogas slurry containing high concentration of ammonia nitrogen is diluted to 128 mg/L of ammonia nitrogen, and 26.2 mg/L of phosphates. The prepared 1000 mL of biogas slurry is added into the biogas slurry storage tank, 1000 mL of microalgae liquid containing 0.1 g/L of *C. sorokiniana* is added into the microalgae cultivating tank. A complete set of the equipment is placed in the illumination incubator, the temperature inside the incubator is set at 25° C., and the intensity of illumination is 7200 Lux. 1 L/L·min of air is fed into the microalgae cultivating tank by air pump. Microalgae flows circularly outside the membrane driven by a peristaltic pump at the circulation flow velocity of 150~160 mL/min, and biogas slurry maintains flowing circularly in the hollow fiber membrane at flow rate of 50~60 mL/min. After 9 days of culture, ammonia nitrogen of treated biogas slurry is decreased to 72.2 mg/L, and phosphates is decreased to 9.2 mg/L.

The parameters of biogas slurry concentration, microalgae concentration, illumination, temperature, ventilation volume etc are maintained the same as those of above, microalgae *C. sorokiniana* and biogas slurry are mixed directly in a general photobioreactor (photobioreactor, PBR), nitrogen and phosphorus that are out of limits therein are treated. After 9 days of culture, ammonia nitrogen of treated biogas slurry is decreased to 102.3 mg/L, phosphates is decreased to 20.7 mg/L, the rate of treating biogas slurry is apparently decreased.

Figure 2:
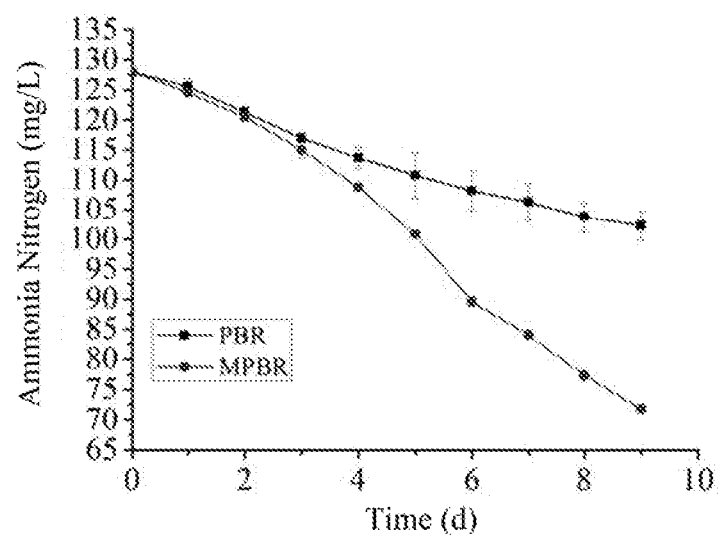
FIG. 2 is the comparison of ammonia nitrogen absorption between the membrane photobioreactor for treating nitrogen and phosphorus that are out of limits in biogas slurry of the present invention and a general photobioreactor.
Figure 3:
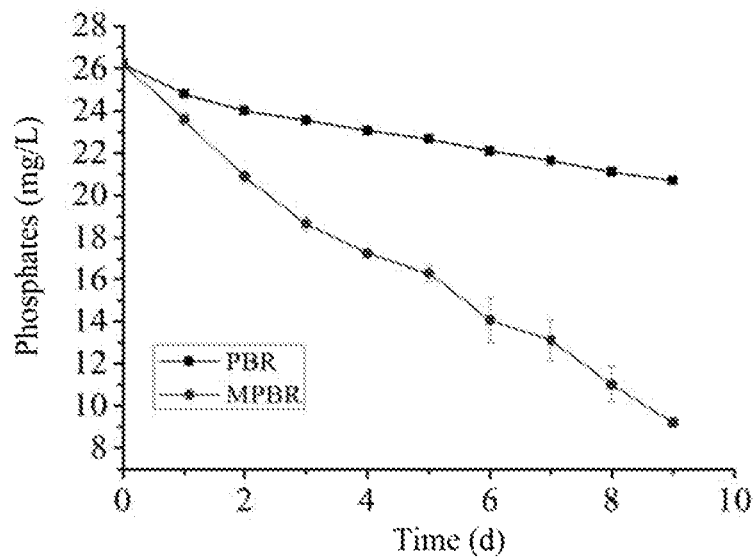
FIG. 3 is the comparison of the phosphates absorption between membrane photobioreactor for treating nitrogen and phosphorus that are out of limits in biogas slurry of the present invention and a general photobioreactor.

See FIG. 2 for the comparison of ammonia nitrogen absorption between the membrane photobioreactor and the general photobioreactor, and see FIG. 3 for the comparison of phosphates absorption between the membrane photobioreactor and the general photobioreactor.

EXAMPLE 2

In a membrane photobioreactor (membrane biophotoreactor, MPBR), primarily, the concentration of biogas slurry containing high concentration of ammonia nitrogen is diluted to 128 mg/L of ammonia nitrogen, and 26.2 mg/L of phosphates. The prepared 1000 mL of biogas slurry is added into the biogas slurry storage tank, 1000 mL of microalgae liquid containing 0.1 g/L of *C. sorokiniana* is added into the microalgae cultivating tank. A complete set of the equipment is placed in the illumination incubator, the temperature inside the incubator is set at 25° C., and the intensity of illumination is 7200 Lux. 1 L/L·min of air is fed into the microalgae cultivating tank by air pump. Microalgae flows circularly outside the membrane driven by peristaltic pump at the circulation flow velocity of 120~140 mL/min, and biogas slurry maintains flowing circularly in the hollow fiber membrane at flow rate of 40~50 mL/min. Undergoing the first day to the $9^{th}$ day of the first batch of culture for 9 days, ammonia nitrogen of treated biogas slurry is decreased to 72.2 mg/L, and phosphates is decreased to 9.2 mg/L.

The parameters of biogas slurry concentration, illumination, temperature, ventilation volume, circulation flow velocity etc are maintained the same as those of the previous batch, the biogas slurry of the same volume is replaced in the biogas slurry storage tank with no change in the microalgae cultivating tank, continue the $10^{th}$ day to the $18^{th}$ day of the second batch culture. Only after 9 days of culture, ammonia nitrogen of the treated biogas slurry is decreased to 51.4 mg/L, and phosphates is decreased to 2 mg/L, the rate for microalgae treating biogas slurry is apparently increased.

Figure 4:
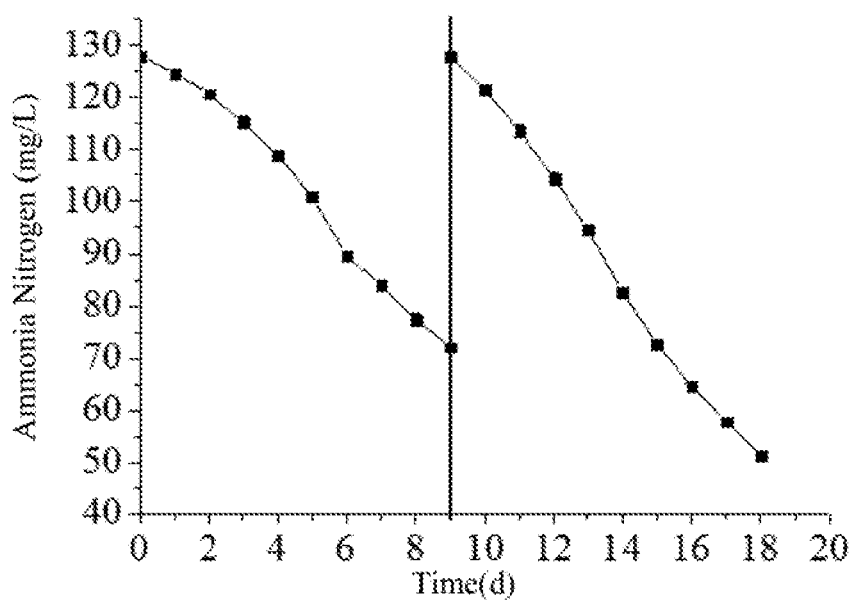
FIG. 4 is the comparison of ammonia nitrogen absorption between the former and the latter batches in the membrane photobioreactor for treating nitrogen and phosphorus that are out of limits in biogas slurry during continuous culture.
Figure 5:
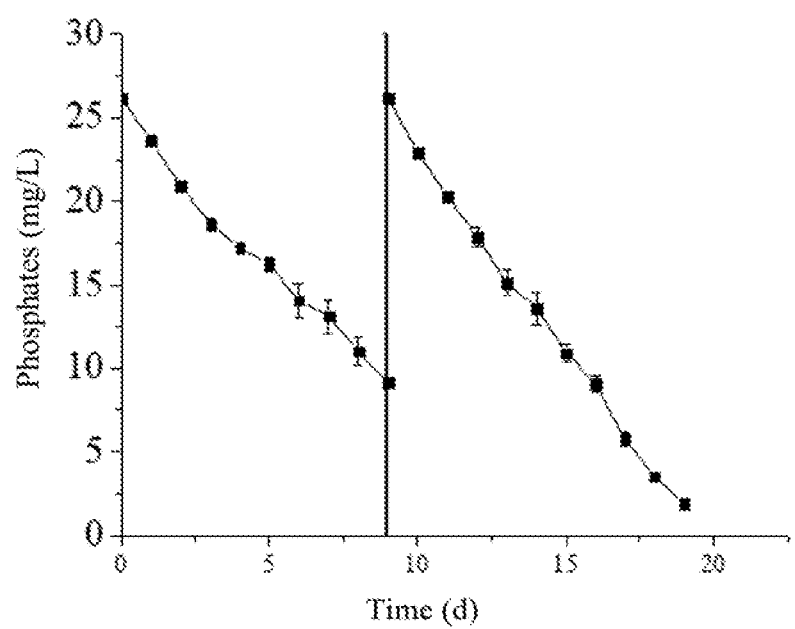
FIG. 5 is the comparison of phosphates absorption between the former and the latter batches in the membrane photobioreactor for treating nitrogen and phosphorus that are out of limits in biogas slurry during continuous culture.

See FIG. 4 for the comparison of ammonia nitrogen absorption between the former and the latter batches in the membrane photobioreactor during continuous culture, and see FIG. 5 for the comparison of phosphates absorption between the former and the latter batches in the membrane photobioreactor during continuous culture.

The invention claimed is:

1. A method for treating biogas slurry, comprising:
   providing an apparatus which includes:
   a biogas slurry storage tank;
   a first peristaltic pump;
   a microalgae cultivating tank having an outlet;
   a second peristaltic pump having an inlet and an outlet, the outlet of the second peristaltic pump connected to the microalgae cultivating tank;
   an air pump having an air outlet that is connected to the microalgae cultivating tank;
   a membrane photobioreactor having:
      an inlet and an outlet at respective side ends, the outlet of the microalgae cultivating tank connected to the inlet at the respective side end of the membrane photobioreactor, and the inlet of the second peristaltic pump connected to the outlet at the respective side end of the membrane photobioreactor; and
      an inlet and an outlet at respective upper and lower ends, the biogas slurry storage tank connected to the inlet and the outlet at the respective upper and lower ends of the membrane photobioreactor; and
   a hollow fiber membrane that is embedded in the membrane photobioreactor, wherein, the membrane photobioreactor is a cylindrical photobioreactor, and a height-to-diameter ration of the cylindrical photobioreactor is 6 to 7, the hollow fiber membrane adopts a 0.1 μm hollow fiber membrane, microalgae solution flows circularly between the microalgae cultivating tank and the membrane photobioreactor driven by the second peristaltic pump, and the microalgae solution is on an outer side of the hollow fiber membrane in the membrane photobioreactor, and wherein a biogas slurry flows circularly between the biogas slurry storage tank and the membrane photobioreactor driven by the first peristaltic pump, and the biogas slurry is on an inner side of the hollow fiber membrane in the membrane photobioreactor;
   storing the biogas slurry which contains ammonia nitrogen and phosphates in the biogas slurry storage tank, the biogas slurry flowing circularly inside a first group of silicone tubes driven by the first peristaltic pump;
   culturing the microalgae solution under illumination in the microalgae cultivating tank, the microalgae solution flowing circularly inside a second group of silicone tubes driven by the second peristaltic pump;
   feeding air into the microalgae cultivating tank by the air pump;
   converging the biogas slurry and the microalgae solution in the membrane photobioreactor;
   circularly flowing the biogas slurry inside the hollow fiber membrane;
   circularly flowing the microalgae solution outside the hollow fiber membrane, the biogas slurry and the microalgae solution being in a cross flow; and
   penetrating the ammonia nitrogen and phosphates in the biogas slurry through the hollow fiber membrane, the ammonia nitrogen and phosphates absorbed by the microalgae solution outside the hollow fiber membrane, the ammonia nitrogen and phosphates in the biogas slurry being absorbed via cyclical cultivation at completion of the absorption of the ammonia nitrogen and phosphates in the biogas slurry in the biogas slurry storage tank, wherein the biogas slurry in the biogas slurry storage tank is replaceable without replacing the microalgae solution in the microalgae cultivating tank,
   wherein, a circulation flow rate of the biogas slurry flowing circularly inside the first group of silicone tubes driven by the first peristaltic pump is 40 to 60 mL/min, and a circulation flow rate of the microalgae solution flowing circularly inside the second group of silicone tubes driven by the second peristaltic pump is 120 to 160 mL/min.

2. The method for treating biogas slurry of claim 1, wherein, the biogas slurry is waste liquid generated after anaerobic fermentation of straw and pig manure producing biogas.

3. The method for treating biogas slurry of claim 1, wherein, an amount of the fed air is 1 liter air per liter microalgae solution per minute.

* * * * *

UNITED STATES PATENT AND TRADEMARK OFFICE
CERTIFICATE OF CORRECTION

PATENT NO. : 10,533,148 B2
APPLICATION NO. : 15/306398
DATED : January 14, 2020
INVENTOR(S) : Li et al.

It is certified that error appears in the above-identified patent and that said Letters Patent is hereby corrected as shown below:

On the Title Page

Item (71) Applicant:
"XIAMEN UNIVERSITY, Xiamen (CN)" should read --XIAMEN UNIVERSITY, Xiamen City (CN)--.

Item (72) Inventors:
"Qingbao Li, Xiamen (CN);" should read --Qingbao Li, Xiamen City (CN);--.

Item (72) Inventors:
"Xi Chen, Xiamen (CN);" should read --Xi Chen, Xiamen City (CN);--.

Item (72) Inventors:
"Ning He, Xiamen (CN);" should read --Ning He, Xiamen City (CN);--.

Item (72) Inventors:
"Yuanpeng Wang, Xiamen (CN);" should read --Yuanpeng Wang, Xiamen City (CN);--.

Item (72) Inventors:
"Liang Shen, Xiamen (CN);" should read --Liang Shen, Xiamen City (CN);--.

Item (72) Inventors:
"Haitao Wang, Xiamen (CN);" should read --Haitao Wang, Xiamen City (CN);--.

In the Claims

Claim 1, Column 7, Line 27:
"a height-to-diameter ration of the cylindrical photo" should read --a height-to-diameter ratio of the cylindrical photo--.

Signed and Sealed this
Seventeenth Day of March, 2020

Andrei Iancu
*Director of the United States Patent and Trademark Office*